United States Patent [19]

Collis, Jr.

[11] Patent Number: 4,660,557
[45] Date of Patent: Apr. 28, 1987

[54] SURGICAL INSTRUMENT

[76] Inventor: John S. Collis, Jr., c/o 29001 Cedar Rd., Cleveland, Ohio 44124

[21] Appl. No.: 722,168

[22] Filed: Apr. 11, 1985

Related U.S. Application Data

[63] Continuation-in-part of Ser. No. 621,606, Jun. 18, 1984.

[51] Int. Cl.⁴ .............................................. A61F 17/32
[52] U.S. Cl. ................... 128/305; 15/236 R; 15/303; D24/28
[58] Field of Search .............. 128/305, 92 XJ, 303 R, 128/304; 30/169, 172; 15/236; D8/14, 107, 101, 90; D24/26, 8, 28, 33; 408/226, 211, 227, 199

[56] References Cited

U.S. PATENT DOCUMENTS

| | | | |
|---|---|---|---|
| D. 272,648 | 2/1984 | Bolesky et al. | D24/28 |
| D. 273,806 | 5/1984 | Bolesky et al. | D24/28 |
| 3,716,057 | 2/1973 | Rubin | 128/305 |
| 3,945,117 | 3/1976 | Beaver | 128/305 |
| 4,211,222 | 9/1980 | Detsch | 128/304 |
| 4,467,801 | 8/1984 | Whiteside | 128/303 R |
| 4,473,070 | 9/1984 | Matthews et al. | 128/92 XJ |
| 4,545,374 | 10/1985 | Jacobson | 128/303 R |

OTHER PUBLICATIONS

V. Mueller & Co., Hospital Supplies & Equipment, ©1930, Item #X1469, p. 149, Medulla Reamer with T. Shaped Handle.
Zimmer-Medical/Surgical Products, ©1981, Item #4033-21, Taper Reamer, p. A 72.
Zimmer-Medical/Surgical Products ©1981, Item #8504-382 Reamer, p. A164.

Primary Examiner—Richard J. Apley
Assistant Examiner—H. Macey
Attorney, Agent, or Firm—Pearne, Gordon, McCoy & Granger

[57] ABSTRACT

A surgical instrument is especially adapted for use in various surgical procedures including use in removing disk material between vertebrae. The instrument has a handle and a flat working portion or body. The edges adjacent to the corners at the forward end of the body are sharpened to provide the cutting edges. The instrument is placed between the vertebrae and rotated back and forth to remove disk material.

14 Claims, 3 Drawing Figures

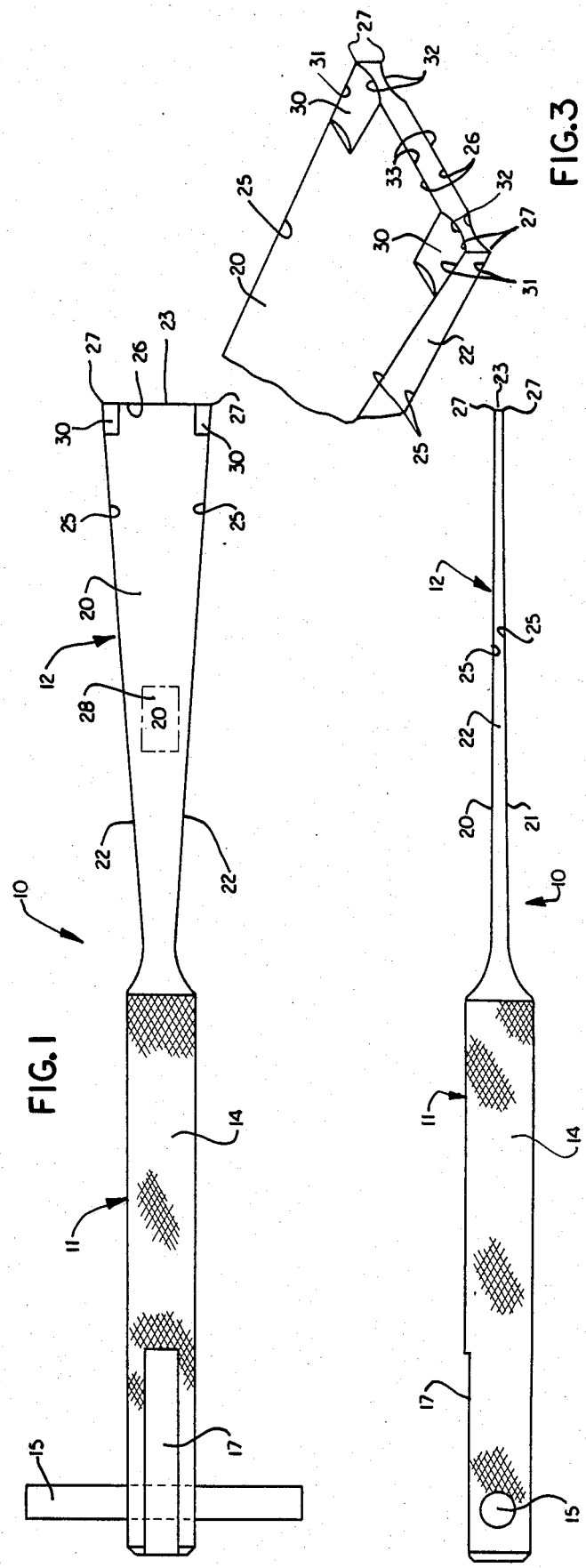

SURGICAL INSTRUMENT

RELATED APPLICATION

This is a continuation-in-part of design application Ser. No. 621,606 filed June 18, 1984.

BACKGROUND OF THE INVENTION

1. Field of the Invention

This invention relates to medical instruments, and more particularly to surgical instruments, such as reamers for removing bone or tissue by rotating the instrument back and forth.

2. Description of the Prior Art

A recently developed technique for repairing ruptured vertebrae disks involves a replacement of the disk material with substitute bone material. As part of this technique, it is necessary to remove the disk material carefully between the vertebrae.

Prior instruments for removal of this material were inadequate in thorough removal of the material from the space between the vertebrae and therefore inefficient in removing of the disk material so that the surgery takes longer than necessary.

There is a need for an instrument to perform the disk removal procedure thoroughly and efficiently so that disk replacement surgery can be conducted safely, effectively and efficiently.

SUMMARY OF THE INVENTION

The present invention provides a surgical instrument which can be used for various surgical procedures including removal of disk material between vertebrae which provides advantages over the prior art surgical instruments and provides the capability of performing disk replacement surgery effectively and efficiently. The instrument of the present invention has a flat forward working portion with cutting edges located only adjacent to the leading corners. The other edges are made dull to avoid the cutting of tissues other than at the corners of the instrument. By rotating the instrument within the space between the vertebrae, the cutting edges at the corners of the instrument effectively cut away the desired disk material. In this manner, disk material may be removed efficiently and effectively.

The instrument of the present invention may be made in a variety of widths so that the disk can be gradually removed using wider and wider sized instruments. For example, initially a very narrow instrument can be used and inserted between the vertebrae and rotated to remove a first layer of disk material therebetween. Following the use of the first instrument, a wider instrument can be inserted to remove an additional layer of disk material. This procedure can be continued until all of the disk material is removed. A series of surgical instruments is thus used with a narrower instrument being used with and progressively wider instruments being used, the width of the final instrument used depending upon the width of the space between the vertebrae where the disk material is being removed.

By placing the cutting edges only at the corners, the instrument of the present invention permits the removal of additional disk material at each step with special additional disk material at each step with special control so that no other matter is removed. After all of the disk material is removed, it is not necessary to employ any further instruments which would otherwise damage the vertebrae or cause problems with other tissue in the spinal area.

The instrument of the present invention is also capable of other surgical uses in addition to use in removing disks.

These and other advantages are achieved by the surgical instrument of the present invention. The surgical instrument comprises a handle and a body extending from the handle. The body has top and bottom surfaces, each substantially flat. Each of the top and bottom surfaces has a forward edge at the end opposite the handle and each has a side edge along each side. The intersection of each forward edge and each side edge forms a forward end corner. The body also has side surfaces, each connecting the adjacent side edges of the top and bottom surfaces. The body also has a foward end surface connecting the forward edges of the top and bottom surfaces. A portion of each of the forward edges extending from each of the forward end corners is sharpened to provide cutting edges. The remaining portions of the forward edges are dulled.

Thus, cutting is performed only with the portion of the forward edges extending from each forward end corner while the remaining portions of the forward edges and portions of the side edges away from the forwarding corners are purposely made dull or blunted to avoid providing a cutting edge. In addition, a portion of each of the end edges extending from each of the foward end corners may be sharpened to provide cutting edges while the remaining portions of the side edges are blunted.

Preferably, the side surfaces diverge away from each other from the handle toward the forward edge. This provides a tapered contruction in which the forward end of the instrument is wider than the portion of the instrument adjacent to the handle to provide ease of insertion of the instrument during surgery.

BRIEF DESCRIPTION OF THE DRAWINGS

FIG. 1 is a top plan view of the instrument of the present invention;

FIG. 2 is a side elevational view of the instrument of FIG. 1; and

FIG. 3 is a detailed perspective view of the forward end of the instrument of FIGS. 1 and 2.

DETAILED DESCRIPTION OF THE PREFERRED EMBODIMENT

Referring more particularly to the drawings, there is shown a surgical instrument 10 according to the present invention. The surgical instrument 10 comprises a cylindrical T-shaped handle 11 and a generally flat working portion or body 12.

The handle comprises a shank portion 14 and a cross bar 15. The shank portion 14 is knurlled to assist in gripping the instrument and includes a flat portion or key 17 extending longitudinally along the shank portion 14 from the end of the handle opposite of the body 12. The key 17 assists the surgeon in providing a tactile means of determining the orientation of the flat body 12. The plane of the key 17 extends generally parallel to the plane of the flat body 12. The cross bar 15 extends through an opening in the shank portion 14 near the end of the handle opposite the body 12. The cross bar 15 extends from the handle and assists the surgeon in rotating the instrument during the surgical procedure. The cross bar 15 should extend from the shank portion 14 in the direction generally parallel to the plane of the body 12. The cross bar 15 extends perpendicular to the shank portion 14.

The body 12 comprises identical top and bottom surfaces 20 and 21 which are generally parallel to each other. The top and bottom surfaces 20 and 21 are separated by side surfaces 22 extending generally perpendicular to both the top and bottom surfaces 20 and 21 along each side of the body 12 and a forward end surface 23 extending generally perpendicular to both the top and bottom surfaces along the forward end of the body 12. The intersection of each of the top and bottom surfaces 21 with each of the side surfaces 22 form side edges 25, there being four such side edges 25. The intersection of each of the top and bottom surfaces with the forward end surface form forward edges 26, there being two such forward edges 26. The intersection of each of the side edges 25 with each of the forward edges 26 forms a forward end corner 27, there being four such forward end corners 27.

The forward portions of the top and bottom surfaces 20 and 21 are generally trapezoidal in shape. The side edges 25 on each side of each of the top and bottom surfaces 20 and 21 diverge away from each other from the portion of the body 12 nearer the handle 11 toward the forward end of the body. Thus, the body 12 tapers inwardly from the forward end toward the handle 11. The widest portion of the body 12 is at the forward end, the body 12 narrowing toward the handle 11.

While the top and bottom surfaces 20 and 21 are generally parallel to each other, the side edges 25 extending along the top and bottom of each side surface 22 preferably converge toward each other in the direction from the handle toward the foward end of the body 12. Thus, the thickness of the body 12 decreases slightly from the handle 11 to the forward end.

The body 12 is generally flat in shape with the width of the top and bottom surfaces 20 and 21 substantially greater than the thickness of the body 12 as represented by the width between the side surfaces 22 at the forward end surface 23. The width of the forward end of the body 12 will vary depending upon the size of the instrument. It is contemplated that a series of instruments would be needed to perform the surgical procedure with the width of the body 12 varying between 8 mm and 20 mm. For example, the surgeon may start with a narrower size instrument having a width of 8 mm to remove a portion of the disk material, and progress using instruments with greater widths until all of the disc material is removed. The thickness of the instrument at the forward end as represented by the width of the forward end surface 23 should only be approximately 2 mm. Thus, with a smaller size instrument having a body width of 8 mm, the width of the instrument is approximately four times the thickness of the instrument at the forward end of the body 12. With a instrument having a width of 20 mm, the width of the instrument may be as much as ten times the thickness of the instrument of the forward end of the body. Preferably, the top surface 20 has a marking portion 28 upon which is marked an indication of the width of the particular instrument. In FIG. 1, a 20 mm instrument is represented with the marking "20" in the portion 28.

The location of the cutting edges of the instrument can best be seen with reference to FIG. 3. Adjacent to each of the four forward end corners 27 is a recess 30, the edges of which form the cutting portions of the instrument. The portion 31 of each of the side edges 25 bordering the recess 30 is sharper than the other portions of the side edges 25. Likewise, a portion 32 of each of the forward edges 26 bordering each recess 30 is sharpened while the remaining portions 33 of each forward edge are made less sharp. Preferably, the edges of the portions 33 are broken off to dull these edges and make them less sharp. Thus, the cutting edges of the instrument are formed along a portion 31 of each of the side edges 25 extending from each of the forward end corners 27, and cutting edges are formed along portion 32 of each of the forward edges 26 extending from each of the forward ends corners which are sharpened while the remaining portions 33 of the forward edges are blunted.

In using the surgical instrument 10, the surgeon inserts the narrowest instrument desired into the space between the vertebrae and rotates the instrument about its longitudinal axis, holding the instrument by the shank portion 14 of the handle 1 and using the cross bar 15 to assist in the rotation of the instrument. As the instrument is rotated back and forth in the space, the cutting edges 31 and 32 at the forward end corners 27 of the body 12 work to remove the desired bone or disk material. Since the other edges of the body 12 are not sharp, the cutting of the other tissue material is avoided.

The instrument can also be used in other surgical procedures in which tissue is to be removed in a controlled manner.

While the invention has been shown and described with respect to a particular embodiment thereof, this is for the purpose of illustration rather than limitation, and other variations and modifications of the specific embodiment herein shown and described will be apparent to those skilled in the art all within the intended spirit and scope of the invention. Accordingly, the patent is not to be limited in scope and effect to the specific embodiment herein shown and described nor in any other way that is inconsistent with the extent to which the progress in the art has been advanced by the invention.

What is claimed is:

1. A surgical instrument comprising:
   a handle; and
   a body extending from the handle, the body having:
   top and bottom surfaces, each substantially flat, each of the top and bottom surfaces having a forward edge at the end opposite the handle, each of the top and bottom surfaces also having a side edge along each side, the intersection of each forward edge and each side edge forming a forward end corner;
   side surfaces each connecting the adjacent side edges of the top and bottom surfaces; and
   a forward end surface connecting the forward edges of the top and bottom surfaces, a portion of each of the forward edges adjoining each of the forward end corners sharpened to provide cutting edges, the remaining portions of the forward edges dulled.

2. A surgical instrument as defined in claim 1, wherein the side surface diverge away from each other from the handle toward the forward edge.

3. A surgical instrument as defined in claim 1, wherein the top and bottom surfaces converge from the handle toward the forward edge.

4. A surgical instrument as defined in claim 1, wherein the distance between the side edges at the forward edge is at least four times greater than the distance between the forward edges.

5. A surgical instrument as defined in claim 1, wherein the top and bottom surfaces are generally parallel to each other.

6. A surgical instrument as defined in claim 1, wherein each of the side surfaces extends generally perpendicular to the top and bottom surfaces.

7. A surgical instrument comprising:
a handle; and
a body extending from the handle, the body having:
top and bottom surfaces, each substantially flat, each of the top and bottom surfaces having a forward edge at the end opposite the handle, each of the top and bottom surfaces also having a side edge along each side, the intersection of each forward edge and each side edge forming a forward end corner;
side surfaces each connecting the adjacent side edges of the top and bottom surfaces, a portion of the side edges sharpened to provide cutting edges, the remaining portions of the side edges left without being sharpened; and
a forward end surface connecting the forward edges of the top and bottom surfaces, a portion of each of the forward edges sharpened to provide cutting edges, the remaining portions of the forward edges dulled.

8. A surgical instrument comprising:
a handle; and
a body extending from the handle, the handle comprising a shank portion extending from the body and a cross bar extending perpendicular to the shank portion, the body having:
top and bottom surfaces, each substantially flat, each of the top and bottom surfaces having a forward edge at the end opposite the handle, each of the top and bottom surfaces also having a side edge along each side, the intersection of each forward edge and each side edge forming a forward end corner;
side surfaces each connecting the adjacent side edges of the top and bottom surfaces; and
a forward end surface connecting the forward edges of the top and bottom surfaces, a portion of each of the forward edges sharpened to provide cutting edges, the remaining portions of the forward edges dulled.

9. A surgical instrument comprising:
a handle; and
a body extending from the handle, the body having:
top and bottom surfaces, each substantially flat and generally parallel to each other, each of the top and bottom surfaces having a forward edge at the end opposite the handle and each having a side edge along each side, the intersection of each forward edge and each side edge forming a sharp forward end corner;
side surfaces each connecting one of the side edges of one of the top and bottom surfaces with the adjacent side edge of the other of the top and bottom surfaces, each of the side surfaces extending generally perpendicular to the top and bottom surfaces; and
a forward end surface connecting the forward edge of one of the top and bottom surfaces with the forward edge of the other of the top and bottom surfaces, a portion of each of the side edges adjoining each of the forward end corners sharpened to provide cutting edges, the remaining portions of the side edges being left without being sharpened.

10. A surgical instrument as defined in claim 9, wherein the side surfaces diverge away from the handle toward the forward edge.

11. A surgical instrument as defined in claim 9, wherein the top and bottom surfaces converge from the handle toward the forward edge.

12. A surgical instrument as defined in claim 9, wherein the distance between the side edges at the forward edge is at least four times greater than the distance between the forward edges.

13. A surgical instrument comprising:
a handle; and
a body extending from the handle, the body having:
top and bottom surfaces, each substantially flat and generally parallel to each other, each of the top and bottom surfaces having a forward edge at the end opposite the handle and each having a side edge along each side, the intersection of each forward edge and each side edge forming a forward end corner;
side surfaces each connecting one of the side edges of one of the top and bottom surfaces with the adjacent side edge of the other of the top and bottom surfaces, each of the side surfaces extending generally perpendicular to the top and bottom surfaces; and
a forward end surface connecting the forward edge of one of the top and bottom surfaces with the forward edge of the other of the top and bottom surfaces, a portion of the forward edges extending from each of the forward end corners sharpened to provide cutting edges while the remaining portions are not, a portion of each of the side edges extending from each of the forward end corners sharpened to provide cutting edges, the remaining portions of the side edges being left without being sharpened.

14. A surgical instrument comprising:
a handle; and
a body extending from the handle, the handle comprising a shank portion extending from the body and a cross bar extending perpendicular to the shank portion,
the body having:
top and bottom surfaces, each substantially flat and generally parallel to each other, each of the top and bottom surfaces having a forward edge at the end opposite the handle and each having a side edge along each side, the intersection of each forward edge and each side edge forming a forward end corner;
side surfaces each connecting one of the side edges of one of the top and bottom surfaces with the adjacent side edge of the other of the top and bottom surfaces, each of the side surfaces extending generally perpendicular to the top and bottom surfaces; and
a forward end surface connecting the forward edge of one of the top and bottom surfaces with the forwrad edge of the other of the top and bottom surfaces, a portion of each of the side edges extending from each of the forward end corners sharpened to provide cutting edges, the remaining portions of the side edges being left without being sharpened.

* * * * *

UNITED STATES PATENT AND TRADEMARK OFFICE
CERTIFICATE OF CORRECTION

PATENT NO. : 4,660,557

DATED : April 28, 1987

INVENTOR(S) : John S. Collis, Jr.

It is certified that error appears in the above-identified patent and that said Letters Patent is hereby corrected as shown below:

Column 1, line 58, change "with" to --first--.

Column 4, line 18, change "1" to --11--.

Column 6, line 62, claim 14, change "forwrad" to --forward--.

Signed and Sealed this

Twelfth Day of January, 1988

*Attest:*

DONALD J. QUIGG

*Attesting Officer*  *Commissioner of Patents and Trademarks*